(12) United States Patent
Fossum et al.

(10) Patent No.: US 6,504,028 B2
(45) Date of Patent: Jan. 7, 2003

(54) PROCESS FOR PREPARING BENZOXAZIN-4-ONE POLYMER CONJUGATES

(75) Inventors: Renae Dianna Fossum, Middletown, OH (US); Todd Laurence Underiner, Cincinnati, OH (US)

(73) Assignee: The Procter & Gamble Co., Cincinnati, OH (US)

(*) Notice: Subject to any disclaimer, the term of this patent is extended or adjusted under 35 U.S.C. 154(b) by 21 days.

(21) Appl. No.: 09/891,475

(22) Filed: Jun. 26, 2001

(65) Prior Publication Data

US 2002/0028934 A1 Mar. 7, 2002

Related U.S. Application Data

(60) Provisional application No. 60/217,521, filed on Jul. 11, 2000.

(51) Int. Cl.$^7$ .................... C07D 265/12; C07D 265/26
(52) U.S. Cl. ........................................... 544/93; 544/94
(58) Field of Search ..................... 544/93, 94

(56) References Cited

U.S. PATENT DOCUMENTS 4,745,116 A * 5/1988 Krantz et al. ................ 544/93
5,428,021 A * 6/1995 Hiebert et al. ................ 514/18

FOREIGN PATENT DOCUMENTS

CA 2065191 * 10/1992

OTHER PUBLICATIONS

Hedstrom et al, "Suicide Inactivation of Chymotrypsin by Benzoxazinones" Biochemistry, vol. 23, pp. 1759–1759 (1984).*

* cited by examiner

*Primary Examiner*—Mukund J. Shah
*Assistant Examiner*—Zachary C. Tucker
(74) *Attorney, Agent, or Firm*—Richard S. Echler, Sr.

(57) ABSTRACT

The present invention relates to a process for forming polymer conjugates which are useful as enzyme inhibitors. The process of the present invention comprises the steps of:

a) reacting a polymer or copolymer alcohol to form a chloroformate;

b) combining a substituted or unsubstituted anthranilic acid comprising an enzyme interaction attenuating unit; and a base catalyst wherein the base catalyst is a supported base catalyst, to form a substrate reactive admixture; and c) adding to said chloroformate formed in step (a) said substrate reactive admixture formed in step (b) to form a benzoxazin-4-one conjugate.

31 Claims, No Drawings

PROCESS FOR PREPARING BENZOXAZIN-4-ONE POLYMER CONJUGATES

CROSS REFERENCE

This Application claims priority to United States Provisional Patent Application Ser. No. 60/217,521 filed Jul. 11, 2000.

FIELD OF THE INVENTION

The present invention relates to an improved process for the preparation of benzoxazin-4-one polymer conjugates. The process of the present invention provides for one-pot high yield conversion of an anthranilate and a polymeric component to proteolytic and/or lipolytic enzyme inhibitors useful in preventing skin irritation caused by endogenic proteolytic and/or lipolytic enzymes, inter alia, trypsin, chymotrypsin, elastase, pancreatic lipase, which comprise human feces.

BACKGROUND OF THE INVENTION

Man-made enzyme inhibitors are widely used to modulate or inhibit the activity of enzymes. Control of enzymes has become critical in the prevention of skin irritation which is caused by the exposure of human skin to endogenic or exogenic enzymes. Particularly infants and incontinent adults have their skin routinely exposed to urine and feces which comprise proteolytic and/or lipolytic enzymes, inter alia, trypsin, chymotrypsin, elastase, pancreatic lipase. These enzymes promote skin degradation and therefore, might lead to discomfort.

Certain enzyme inhibitors have been successfully combined with polymeric materials to form benzoxazin-4-one polymer conjugates which modulate enzyme activity on exposed human skin while simultaneously providing the benefit of not being absorbed into the skin of the user. The process for preparing these polymer conjugates involves several discrete synthetic steps each of which involves isolation of a reaction intermediate or the use of reagents or solvents which present safety and cost issues.

There is therefore a long felt need for a process for forming a benzoxazin-4-one polymer conjugate which provides a direct, cost effective, and safe route.

SUMMARY OF THE INVENTION

The present invention meets the aforementioned needs in that it has been surprisingly discovered that benzoxaxine-4-one polymer conjugates can be prepared by way of a direct synthesis which provides the formulator with a more facile, cost effective, and safer route. The improvement over our own prior art synthesis precludes the use of more hazardous solvents, inter alia, methylene chloride, and affords the desired polymer conjugate in high yield.

The process of the present invention comprises the steps of:

a) reacting a polymer or copolymer having the formula:

R—OH wherein R is a hydrocarbyl moiety, a polyalkyleneoxy moiety, or a heteroatom comprising hydrocarbyl moiety, said polymer or copolymer having a molecular weight of from about 500 daltons, with phosgene to form a chloroformate having the formula:

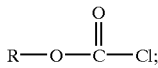

b) combining a substituted or unsubstituted anthranilic acid having the formula:

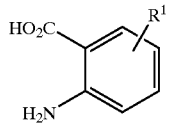

wherein each $R^1$ unit is an enzyme interaction attenuating unit; and a base catalyst wherein said base catalyst is a supported base catalyst, to form a substrate reactive admixture; and c) adding to said chloroformate formed in step (a) said substrate reactive admixture formed in step (b) to form a benzoxazin-4-one conjugate having the formula:

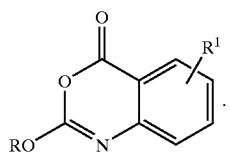

The process of the present invention also relates to the use of an auxiliary chloroformate, inter alia, a lower alkyl chloroformate to affect the benzoxazin-4-one ring closure.

The process of the present invention further relates to reacting a polymer or copolymer having the formula:

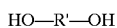

which when reacted with an anthranilate forms a polymer conjugate having two benzoxazin-4-one moieties.

These and other objects, features and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to a process for preparing benzoxazin-4-one polymer conjugates. The following is a description of the essential elements of the present invention.

Step (a): Formation of a chloroformate. Conversion of a hydroxyl moiety comprising polymer or copolymer to a chloroformate is the first required step of the process of the present invention. The polymer or copolymer may comprise one or more hydroxyl moieties thereby yielding a polymer conjugate which comprises more than one benzoxazin-4-one unit. However, the formulator may form the polymer conjugate having more than one hydroxyl unit in a manner wherein only an average of one hydroxyl unit links to a benzoxazin-4-one.

A polymer or copolymer having the general formula:

R—OH wherein R is a hydrocarbyl moiety, a polyalkyleneoxy moiety, or a heteroatom comprising hydrocarbyl moiety, said polymer or copolymer having a molecular weight of from about 500 daltons, is reacted with phosgene to form a chloroformate having the formula:

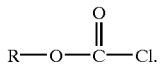

Phosgene in the form of a gas or as a solution, inter alia, 20% solution by weight in toluene. Preferably a stoichiometric amount of phosgene is used. One equivalent of phosgene is used for every equivalent of —OH unit which is present in the polymer or copolymer molecule. For example, a mono-hydroxy polymer or copolymer will require one equivalent of phosgene, however, a polymer or copolymer comprising two —OH moieties, as in the preparation of a bis-benzoxazin-4-one conjugate analog, inter alia, bis-2-(PEG 4000)-5-methyl4H-3,1-benzoxazin-4-one, said formation requires at lease two equivalents of phosgene.

Examples of two preferred embodiments of the present invention relate to reacting a mono-hydroxy containing polymer or copolymer with phosgene to form a mono-chloroformate and reacting a dihydroxy polymer or copolymer with phosgene to form a bis-chloroformate.

The mono-hydroxy polymers or co-polymers of the present invention have the general formula:

R—OH whereas the dihydroxy polymers or co-polymers have the general formula:

HO—R'—OH wherein R' is preferably a polyalkyleneoxy moiety further described herein below, however, for the purposes of the present invention the general formula:

R—OH stands equally well for mono- as well as poly-hydroxy comprising polymers or co-polymers unless otherwise indicated.

For the purpose of the present invention the term "hydrocarbyl moiety" is defined herein as "any organic moiety which is comprised of carbon and hydrogen atoms in addition to the oxygen atoms which comprise the —OH units present. The only heteroatoms or atoms other than carbon and hydrogen are those atoms which are oxygen atoms comprising the hydroxyl moiety or moieties which react with phosgene in the first step of the present invention process."

The polymers or copolymers of the present invention may comprise monomers all of which have a hydroxyl unit, for example the polymer having the general formula:

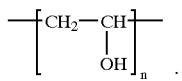

The formulator can include within the scope of the present invention lower molecular weight alcohols which when combined with the enzyme inhibitor elements do not diffuse into the skin cells and are therefore suitable for use as conjugates. Non-limiting examples of lower molecular weight alcohols useful according to the present invention include:

a) $CH_3$—$(CH_2)_{21}$—OH;

b) 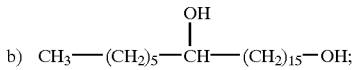

c) HO—$(CH_2)_{36}$—OH;

d) 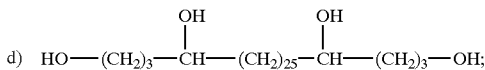
e) 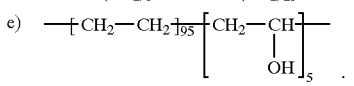

For the purposes of the present invention a "polyalkyleneoxy moiety" is defined herein as a unit having the formula:

$R^2(OR^3)_x$— wherein $R^2$ is hydrogen, $C_1$–$C_{22}$ alkyl, $C_2$–$C_6$ hydroxyalkyl, $C_6$–$C_{12}$ substituted or unsubstituted aryl, and mixtures thereof; preferably hydrogen, $C_1$–$C_4$ alkyl, $C_2$–$C_4$ hydroxyalkyl, said hydroxyalkyl having the formula $HO(CH_2)_{2-4}$-; more preferably hydrogen and methyl.

$R^3$ is $C_2$–$C_{12}$ alkylene, phenylene, $C_1$–$C_4$ alkyl substituted phenylene, $C_7$–$C_{22}$ alkylenearylene, and mixtures thereof; preferably $C_2$–$C_6$ alkylene, more preferably $C_2$–$C_6$ alkylene, yet more preferably ethylene, 1,2-propylene, most preferably ethylene.

The index x has the value from about 10 to about 10,000; preferably x has a value such that the "polyalkyleneoxy moiety" has an average molecular weight of from about 500 daltons, preferably from about 1000 daltons, more preferably from about 2000 daltons, most preferably from about 3000 daltons to about 10,000 daltons, preferably to about 8,000 daltons, more preferably to about 7500 daltons.

Non-limiting examples of suitable polyalkyleneoxy polymers for use in the present invention include polyethyleneglycol having an average molecular weight of 1500 daltons (PEG 1500), 4000 daltons (PEG 4000), polyethyleneglycol having an average molecular weight of 5000 daltons (PEG 5000), polyethyleneglycol methyl ether having an average molecular weight of 1500 daltons (MPEG 1500), polyethyleneglycol methyl ether having an average molecular weight of 4000 daltons (MPEG 4000), polyethyleneglycol methyl ether having an average molecular weigh of 5000 daltons (MPEG 5000), block co-polymers of polyethylene glycol and polypropylene glycol (EO/PO co-polymers, wherein said PO unit can be 1,2-propylene, 1,3-propylene, or mixtures thereof), for example Pluronics® available ex BASF.

For the purposes of the present invention the term "heteroatom comprising hydrocarbyl moiety" is defined herein as any polymer or polymer conjugate which comprises one or more heteroatom, inter alia, nitrogen, other than an oxygen atom as described herein above for the definition of "hydrocarbyl".

Preferred heteroatom units have the formula:

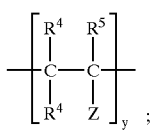

wherein each $R^4$ is independently
a) hydrogen;
b) $C_1$–$C_4$ alkyl;
c) substituted or unsubstituted phenyl;
d) substituted or unsubstituted benzyl;
e) carbocyclic;
f) heterocyclic;
g) and mixtures thereof;
  each $R^5$ is independently
a) hydrogen;
b) halogen
C) $C_1$–$C_4$ alkyl;
d) $C_1$–$C_4$ alkoxy;
e) substituted or unsubstituted phenyl;
f) substituted or unsubstituted benzyl;
g) carbocyclic;
h) heterocyclic;
i) and mixtures thereof;
  each Z is independently
a) hydrogen;
b) hydroxyl;
c) halogen;
d) —$(CH_2)_m R$;
  wherein R is:
    i) hydrogen;
    ii) hydroxyl
    iii) halogen;
    iv) nitrilo;
    V) —$OR^6$;
    vi) or mixtures thereof;
      each $R^6$ is independently hydrogen, $C_1$–$C_8$ alkyl, $C_2$–$C_8$ hydroxyalkyl, and mixtures thereof;
the index m is from 0 to 6.

A non-limiting example of a "heteroatom comprising hydrocarbyl moiety" includes the co-polymer having the formula:

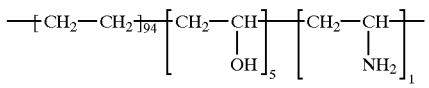

wherein the indices indicate the percentage of each monomer present.

In addition "star polymers" are suitable as the heteroatom containing units. These polymers includ tetra functional block copolymers of polyethylene glycol and polypropylene glycol based on reaction between ethylene diamine and ethylene oxide and polypropylene oxide, for example Tetronics® available ex BASF; trifunctional block copolymers of polyethylene glycol and polypropylene glycol based on reaction between propylene glycol and ethylene oxide and propylene oxide, for example, Poly-G T® series available ex BASF; and hydroxy-terminated Starburst® dendrimer (PAMAM-OH) of generation 2, 3, or 4, available ex Aldrich.

Step (a) of the present invention is preferably conducted in the presence of a solvent although a solvent is not necessary for formation of the chloroformate. Non-limiting examples of solvents include dichloromethane, toluene, benzene, ethyl acetate, and mixtures thereof, preferably dichloromethane and toluene. One preferred embodiment of the present invention utilizes a mixture of solvents, inter alia, dichloromethane and toluene. When a solvent is to be used for step (a), it is convenient to use toluene since phosgene is commercially available as a solution in toluene. However, mixtures of solvents can also be used if necessary to solublize the polymer or copolymer or the resulting chloroformate.

Step (a) is conducted at any temperature which is adequate to facilitate the formation of the desired chloroformate, preferably from 0° C., more preferably from 25° C., most preferably from 40° C. to preferably about 200° C., more preferably about 110° C. The addition of the phosgene can be followed by refluxing of the solution. Typically when the formation of the chloroformate is accompanied by the evolution of excess heat a cooling device can be employed, however, under some circumstances, inter alia, the use toluene as a solvent, it may be necessary to warm the reaction to insure completeness of reaction.

Preferably the source of phosgene is added to the polymer or copolymer, however, any order of addition which adequately forms the chloroformate is encompassed by the present invention. The use of nitrogen, argon, or other suitable gas to provide an inert atmosphere for the reaction of step (a) is optional, but preferred.

Step (b): Combining a substituted or unsubstituted anthranilic acid with a base catalyst. Forming a substrate reactive admixture by combining an anthranilate and a base catalyst is the second required step of the process of the present invention.

A substituted or unsubstituted anthranilic acid having the formula:

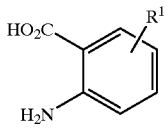

wherein each $R^1$ unit is an enzyme interaction attenuating unit; and a base catalyst wherein said base catalyst is a supported base catalyst, is combined to form a substrate reactive admixture.

Preferably each $R^1$ is independently selected from the group consisting of:
a) hydrogen;
b) $C_1$–$C_{18}$ substituted or unsubstituted, linear or branched alkyl;
c) $C_3$–$C_{18}$ substituted or unsubstituted, linear or branched cycloalkyl
d) $C_2$–$C_{18}$ substituted or unsubstituted, linear or branched alkenyl;
e) $C_2$–$C_{18}$ substituted or unsubstituted, linear or branched alkynyl;
f) $C_6$–$C_{18}$ substituted or unsubstituted aryl;
g) $C_2$–$C_{18}$ substituted or unsubstituted heterocyclic alkyl;
h) $C_3$–$C_{18}$ substituted or unsubstituted heterocyclic alkenyl;
i) alkylenearyl having the formula:

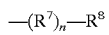

wherein $R^7$ is $C_1$–$C_{12}$ linear or branched alkylene, $C_2$–$C_{12}$ linear or branched alkenylene, or mixtures thereof; $R^8$ is $C_6$–$C_{18}$ substituted or unsubstituted aryl, or mixtures thereof; n is from 1 to 16;

j) an amino unit having the formula:

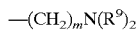

wherein each $R^9$ is independently $C_1$–$C_{18}$ substituted or unsubstituted, linear or branched alkyl; m is from 0 to 10;

k) a unit having the formula:

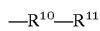

wherein $R^{10}$ is —$(CH_2)_p$—, wherein p is from 0 to 12; $R^{11}$ is:
i) $C_1$–$C_{18}$ substituted or unsubstituted, linear or branched alkyl;
ii) $C_3$–$C_{18}$ substituted or unsubstituted, linear or branched cycloalkyl
iii) $C_2$–$C_{18}$ substituted or unsubstituted, linear or branched alkenyl;
iv) $C_2$–$C_{18}$ substituted or unsubstituted, linear or branched alkynyl;
v) $C_6$–$C_{18}$ substituted or unsubstituted aryl;
vi) $C_2$–$C_{18}$ substituted or unsubstituted heterocyclic alkyl;
vii) $C_3$–$C_{18}$ substituted or unsubstituted heterocyclic alkenyl;
viii) —$OR^{12}$; wherein $R^{12}$ is $C_1$–$C_4$ alkyl, $C_6$–$C_{10}$ aryl;
ix) or mixtures thereof; and l) mixtures thereof.

For the purposes of the present invention $C_2$–$C_{18}$ substituted or unsubstituted heterocyclic alkyl is defined as any ring comprising an atom other than carbon, inter alia, nitrogen, sulfur, oxygen. Non-limiting examples of heterocyclic alkyl rings include, morpholinyl, piperidinyl, pyrrolidinyl.

For the purposes of the present invention $C_3$–$C_{18}$ substituted or unsubstituted heterocyclic alkenyl is defined as any ring comprising a site of unsaturation and an atom other than carbon, inter alia, nitrogen, sulfur, oxygen. Non-limiting examples of heterocyclic alkenyl rings include oxazolyl, 1-pyrrolinyl, and indolyl.

Non-limiting examples of $R^1$ are selected from the group consisting of hydrogen, methyl, ethyl, isopropyl, phenyl, benzyl, amidino, bi-phenyl, —$OR^{12}$; wherein $R^{12}$ is methoxy, and mixtures thereof.

The base catalyst which is used in step (b) of the present invention is preferably a supported base catalyst. Non-limiting examples of supported base catalysts include poly 4-(vinylpyridine), DOWEX basic amine resin, inter alia, DOWEX Marathon WBA® available ex Dow Chemical; Amberlite® IRA-67, Aberlyst® A-21 available ex Rohm and Haas; Duolite® A-7 available ex Aldrich.

Step (b) of the present invention is preferably conducted in the presence of a solvent although a solvent is not necessary. Non-limiting examples of solvents include dichloromethane, toluene, benzene, ethyl acetate, and mixtures thereof, preferably dichloromethane and toluene. One preferred embodiment of the present invention utilizes a mixture of solvents, inter alia, dichloromethane and toluene. When a solvent is to be used for step (b), it is convenient to use toluene since a higher temperature can be used to dissolve reagents. However, mixtures of solvents can also be used if necessary to solublize the anthranilate adduct.

Step (b) is conducted at any temperature which is adequate to facilitate the formation of the desired admixture. The final admixture may be a homogeneous solution or a slurry depending upon the needs of the formulator. One embodiment of the present invention conducts step (b) under anhydrous conditions, that is the reagents are dried or excess moisture is removed before combining.

The use of nitrogen, argon, or other suitable gas to provide an inert atmosphere for the reaction of step (b) is optional, but preferred.

Step (c): Formation of a benzoxazin-4-one conjugate. The reacting of the chloroformate from step (a) with the substrate reactive admixture of step (b) is the third required step of the process of the present invention.

The chloroformate and anthranilate are reacted together in the presence of a base, said base being added in step (b) of the present process. In a preferred process according to the present invention, two equivalents or more of chloroformate may be used for every equivalent of benzoxazin-4-one conjugate formed.

In another preferred embodiment of the present invention, an auxiliary chloroformate is used to facilitate ring closure. Without wishing to be limited by theory, the first equivalent of chloroformate reacts to form a carbamate. A preferred additional step (d) comprises adding an auxiliary chloroformate to an in situ formed carbamate, said carbamate being the reaction product of the chloroformate from step(a) and the anthranilate from step (b). For example, step (c) is conducted wherein one equivalent of a polymer or copolymer chloroformate is added to one equivalent of a substrate reactive admixture under conditions wherein an un-isolated carbamate is formed in situ having the formula:

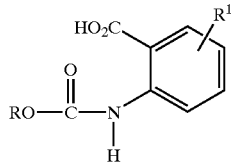

and ethyl chloroformate is then added as an auxiliary chloroformate. Without wishing to be limited by theory, the auxiliary chloroformate reacts with the free carboxyl unit, —$CO_2H$, to form a mixed anhydride thereby facilitating ring closure and formation of the benzoxazin-4-one having the formula:

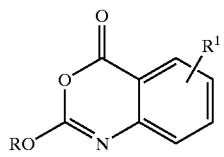

wherein R is a polymer or copolymer moiety.

Step (c) and optional step (d) is conducted at any temperature which is adequate to facilitate the formation of the desired benzoxazin-4-one conjugate, preferably from 50° C. to about 150° C., more preferably to about 75° C. The reagents may be added in any order, for example the chloroformate to the reactive admixture or vice versa. However, when employing step (d), use of an auxiliary chloroformate, the chloroformate from step (a) must be reacted with the anthranilate first. Step (c) and step (d) are preferably conducted under anhydrous conditions, that is steps (a) and (b) are conducted under anhydrous conditions and the conditions are maintained throughout the procedure.

The use of nitrogen, argon, or other suitable gas to provide an inert atmosphere for the reaction of step (c) and (d) is optional, but preferred.

The polymer conjugate once formed is preferably isolated and purified, but isolation and purification is not necessary.

Non-limiting examples of auxiliary chloroformates which are useful in optional step (d) include methyl chloroformate, ethyl chloroformate, isobutyl chloroformate, and the like.

A general example of a preferred embodiment of the present invention comprises the steps of:

a) reacting a polymer or copolymer having the formula:

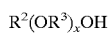

wherein $R^2$ is methyl; $R^3$ is ethylene; x has the value from about 10 to about 225, in the presence of toluene with a solution of phosgene in toluene to form a chloroformate having the formula:

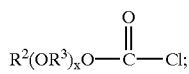

b) combining an anthranilic acid or derivative thereof having the formula:

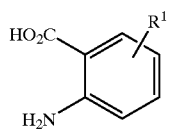

wherein each $R^1$ unit is hydrogen or methyl; and poly 4-vinylpyridine to form a substrate reactive admixture;

c) adding to said substrate reactive admixture formed in step (b) said chloroformate from step (a) to form a benzoxazin-4-one conjugate having the formula:

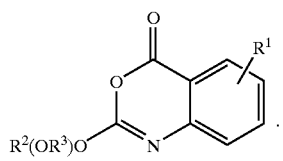

A preferred embodiment of the above process comprises the steps of:

c) adding to one equivalent of said substrate reactive admixture formed in step (b) one equivalent of said chloroformate from step (a) to form a carbamate having the formula:

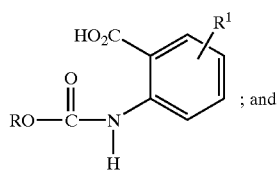
; and d) reacting said carbamate with an auxiliary chloroformate to form a benzoxazin-4-one conjugate having the formula:

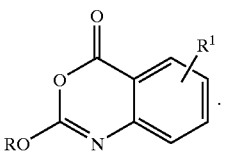

The following are non-limiting examples of the process of the present invention.

EXAMPLE 1

Synthesis of 2-(MPEG 5000)-5-Methyl4H-3.1-benzoxazin-4-one

Methoxy polyethyleneglycol having an average molecular weight of about 5000 daltons (MPEG 5000) (50 g, 0.01 mol) is charged to a reaction vessel and dissolved in dichloromethane (125 mL). Under an inert atmosphere, a solution of phosgene in toluene (5.7 mL, 1.93 M) is added while cooling in ice. After addition, the ice bath is removed and the reaction mixture stirred for 12–18h under an inert atmosphere to form an MPEG 5000 chloroformate. In a separate flask, 2-amino-6-methylbenzoic acid (1.66 g, 0.011 mol) is dissolved in dichloromethane (100 mL) which is heated to 30° C. The heat source is removed and while still warm, poly(4-vinylpyridine) (10.23 g, 0.09 mol) is added to the solvent. With vigorous stirring, the MPEG 5000 chloroformate is added dropwise to the mixture. The reaction mixture is stirred for 12–24 h, then ethyl chloroformate (9.6 mL, 0.1 mol) is added at room temperature and stirred for another 12–24 h. The solution is filtered to remove the poly(4-vinylpyridine) and the solution is precipitated onto 3.5 L of diethyl ether. The precipitate is filtered under nitrogen to yield 2-(MPEG 5000)-5-methyl4H-3,1-benzoxazin-4-one as a white solid (33.3 g, 67%) which is dried under vacuum.

EXAMPLE 2

Synthesis of 2-(MPEG 5000)-5-Methyl-4H-3,1-benzoxazin-4-one in Toluene

Methoxy polyethyleneglycol having an average molecular weight of about 5000 daltons (MPEG 5000) (13.7 g, 2.75 mmol) is charged to a reaction vessel and dissolved in toluene (100 mL) at 48° C. Under an inert atmosphere, a solution of phosgene in toluene (1.6 mL, 1.93M) is added while cooling in ice. After the addition, the reaction mixture is stirred for 12–18 h under an inert atmosphere at 48° C. to form an MPEG 5000 chloroformate. In a separate flask, 2-amino-6-methylbenzoic acid (457 mg, 3.025 mmol) is dissolved in toluene (70 mL) that is heated to 75° C. Poly(4-vinylpyridine) (3.75 g, 0.033 mol) is added to the solution. The MPEG 5000 chloroformate is added dropwise to the anthranilate mixture. The reaction mixture is stirred for 12–24 h, then the temperature is raised to 80° C. and ethyl chloroformate (2.6 mL, 27.5 mmol) is added and reaction mixture is stirred for another 12–24 h. The solution is filtered to remove the poly(4-vinylpyridine) and the solution is precipitated onto 3.5 L of diethyl ether. The precipitate is filtered under nitrogen to yield 2-(MPEG 5000)-5-methyl-4H-3,1-benzoxazin-4-one as a white solid (12.4 g, 90%) which is dried under vacuum.

EXAMPLE 3

Synthesis of bis-2-(PEG 4000)-5-Methyl4H-3,1-benzoxazin-4-one

Polyethylene glycol having an average molecular weight of about 4000 daltons (PEG 4000) (5 g, 1.25 mmol) is charged to a reaction vessel and dissolved in dichloromethane (16 mL). Under an inert atmosphere, a solution of phosgene in toluene (1.6 mL, 1.93M) is added. After addition, the reaction mixture is stirred for 12–18 h to form the PEG-4000 his chloroformate. In a separate flask, 2-amino-6-methylbenzoic acid (416 mg, 2.75 mmol) is dissolved in dichloromethane (25 mL) which is warmed to 30° C. The heat source is removed and while still warm, poly(N-vinylpyridine) (2.13 g, 18.75 mmol) is added to the anthranilate solution. The MPEG bis chloroformate is added dropwise to anthranilate mixture, and the reaction mixture stirred for 12–24h and ethyl chloroformate (1.8 mL, 18.75 mmol) is added at room temperature. The reaction mixture is stirred for 12–24 h. The solution is filtered to remove the poly(N-vinylpyridine) and the solution is precipitated onto 3.5 L of diethyl ether. The precipitate is filtered under nitrogen to yield bis-2-(PEG 4000)-5-methyl4H-3,1 -benzoxazin-4-one as a white solid (4.3 g, 86%) which is dried under vacuum.

What is claimed is:

1. A process comprising the steps of:
   a) reacting a polymer or copolymer having the formula:

wherein R is a hydrocarbyl moiety, a polyalkyleneoxy moiety, or a heteroatom comprising hydrocarbyl moiety, said polymer or copolymer having a molecular weight of from about 500 daltons, with phosgene to form a chloroformate having the formula:

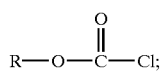

b) combining a substituted or unsubstituted anthranilic acid having the formula:

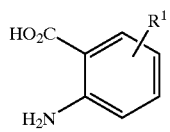

wherein each $R^1$ unit is an enzyme interaction attenuating unit; and a base catalyst wherein said base catalyst is a supported base catalyst, to form a substrate reactive admixture; and
   c) adding to said chloroformate formed in step (a) said substrate reactive admixture formed in step (b) to form a benzoxazin-4-one conjugate having the formula:

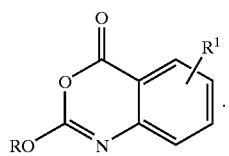

2. A process according to claim 1 wherein said hydrocarbyl moiety is selected from the group consisting of polyethylene, polypropylene, polybutylene, polystyrene, and mixtures thereof.

3. A process according to claim 1 wherein said polyalkyleneoxy moiety has the formula:

wherein $R^2$ is hydrogen, $C_1$–$C_{22}$ alkyl, $C_2$–$C_6$ hydroxyalkyl, $C_6$–$C_{12}$ substituted or unsubstituted aryl, and mixtures thereof; $C_2$–$C_{12}$ alkylene, phenylene, $C_1$–$C_4$ alkyl substituted phenylene, $C_7$–$C_{22}$ alkylenearylene, and mixtures thereof; x has the value from about 10 to about 10,000.

4. A process according to claim 3 wherein $R^2$ is methyl and $R^3$ is $C_2$–$C_6$ alkylene, and mixtures thereof.

5. A process according to claim 4 wherein $R^3$ is ethylene.

6. A process according to claim 3 wherein $R^2$ is selected from the group consisting of $HO(CH_2)_2$—, $HO(CH_2)_3$—, $HO(CH_2)_4$—, and mixtures thereof.

7. A process according to claim 6 wherein $R^2$ is $HO(CH_2)_2$—.

8. A process according to claim 7 wherein $R^3$ is ethylene.

9. A process according to claim 3 wherein $R^3$ is a mixture of ethylene and 1,2-propylene.

10. A process according to claim 1 wherein said heteroatom comprising hydrocarbyl moiety has the formula:

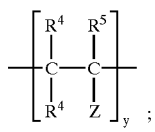

wherein each $R^4$ is independently
    a) hydrogen;
    b) $C_1$–$C_4$ alkyl;
    c) substituted or unsubstituted phenyl;
    d) substituted or unsubstituted benzyl;
    e) carbocyclic;
    f) heterocyclic;
    g) and mixtures thereof;
    each $R^5$ is independently
    a) hydrogen;
    b) halogen
    c) $C_1$–$C_4$ alkyl;
    d) $C_1$–$C_4$ alkoxy;
    e) substituted or unsubstituted phenyl;
    f) substituted or unsubstituted benzyl;
    g) carbocyclic;
    h) heterocyclic;
    i) and mixtures thereof;
    each Z is independently
    a) hydrogen;
    b) hydroxyl;
    c) halogen;
    d) —$(CH_2)_m R$;
       wherein R is:
       i) hydrogen;
       ii) hydroxyl;
       iii) halogen;
       iv) nitrilo;
       v) —$OR^6$;
       vi) or mixtures thereof;
       each $R^6$ is independently hydrogen, $C_1$–$C_8$ alkyl, $C_2$–$C_8$ hydroxyalkyl, and mixtures thereof;
       the index m is from 0 to 6.

11. A process according to claim 1 wherein each $R^1$ is independently selected from the group consisting of:
a) hydrogen;
b) $C_1$–$C_{18}$ substituted or unsubstituted, linear or branched alkyl;
c) $C_3$–$C_{18}$ substituted or unsubstituted, linear or branched cycloalkyl
d) $C_2$–$C_{18}$ substituted or unsubstituted, linear or branched alkenyl;
e) $C_2$–$C_{18}$ substituted or unsubstituted, linear or branched alkynyl;
f) $C_6$–$C_{18}$ substituted or unsubstituted aryl;
g) $C_2$–$C_{18}$ substituted or unsubstituted heterocyclic alkyl;
h) $C_3$–$C_{18}$ substituted or unsubstituted heterocyclic alkenyl;
i) alkylenearyl having the formula:

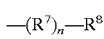

wherein $R^7$ is $C_1$–$C_{12}$ linear or branched alkylene, $C_2$–$C_{12}$ linear or branched alkenylene, or mixtures thereof; $R^8$ $C_6$–$C_{18}$ substituted or unsubstituted aryl, or mixtures thereof; n is from 1 to 16;
j) an amino unit having the formula:

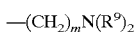

wherein each $R^9$ is independently $C_1$–$C_{18}$ substituted or unsubstituted, linear or branched alkyl; m is from 0 to 10;
n) a unit having the formula:

wherein $R^{10}$ is —$(CH_2)_p$—, wherein p is form 0 to 12; $R^{11}$ is:
  i) $C_1$–$C_{18}$ substituted or unsubstituted, linear or branched alkyl;
  ii) $C_3$–$C_{18}$ substituted or unsubstituted, linear or branched cycloalkyl
  iii) $C_2$–$C_{18}$ substituted or unsubstituted, linear or branched alkenyl;
  iv) $C_2$–$C_{18}$ substituted or unsubstituted, linear or branched alkynyl;
  v) $C_6$–$C_{18}$ substituted or unsubstituted aryl;
  vi) $C_2$–$C_{18}$ substituted or unsubstituted heterocyclic alkyl;
  vii) $C_3$–$C_{18}$ substituted or unsubstituted heterocyclic alkenyl;
  viii) —$OR^{'2}$; wherein $R^{12}$ is $C_1$–$C_4$ alkyl, $C_6$–$C_{10}$ aryl;
  ix) or mixtures thereof; and
o) mixtures thereof.

12. A process according to claim 11 wherein $R^1$ is selected from the group consisting of hydrogen, methyl, ethyl, isopropyl, phenyl, benzyl, amidino, bi-phenyl, —$OR^{12}$; wherein $R^{12}$ is methoxy, and mixtures thereof.

13. A process according to claim 12 wherein $R^1$ is methyl.

14. A process according to claim 12 wherein $R^1$ is hydrogen.

15. A process according to claim 1 wherein step (a) is conducted in the presence of a solvent.

16. A process according to claim 15 said solvent is dichloromethane, toluene, and mixtures thereof.

17. A process according to claim 1 wherein step (b) is conducted in the presence of a solvent.

18. A process according to claim 17 said solvent is dichloromethane, toluene, and mixtures thereof.

19. A process according to claim 1 wherein step (c) is conducted in the presence of a solvent.

20. A process according to claim 19 said solvent is dichloromethane, toluene, and mixtures thereof.

21. A process according to claim 1 wherein said supported base catalyst is poly 4-vinylpyridine.

22. A process according to claim 1 wherein step (a) is conducted at a temperature of from 0° C. to 200° C.

23. A process according to claim 22 wherein step (a) is conducted at a temperature of from 25° C. to 110° C.

24. A process according to claim 23 wherein step (a) is conducted at a temperature of from 40° C. to 110° C.

25. A process according to claim 19 wherein step (a) is refluxed.

26. A process according to claim 1 wherein step (c) is conducted at a temperature of from 50° C. to 150° C.

27. A process according to claim 26 wherein step (c) is conducted at a temperature of from 50° C. to 75° C.

28. A process according to claim 1 further comprising the step:
d) isolating said benzoxazin-4-one conjugate.

29. A process comprising the steps of:
a) reacting a polymer or copolymer having the formula:

R—OH wherein R is a hydrocarbyl moiety, a polyalkyleneoxy moiety, or a heteroatom comprising hydrocarbyl moiety, said polymer or copolymer having a molecular weight of from about 500 daltons, with phosgene to form a chloroformate having the formula:

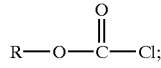

b) combining a substituted or unsubstituted anthranilic acid having the formula:

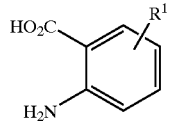

wherein each $R^1$ unit is an enzyme interaction attenuating unit; and a base catalyst wherein said base catalyst is a supported base catalyst, to form a substrate reactive admixture;

c) adding to one equivalent of said substrate reactive admixture formed in step (b) one equivalent of said chloroformate from step (a) to form a carbamate having the formula:

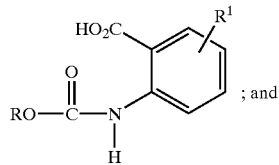

; and d) reacting said carbamate with an auxiliary chloroformate to form a benzoxazin-4-one conjugate having the formula:

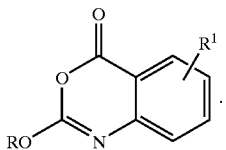

30. A process comprising the steps of:

a) reacting a polymer or copolymer having the formula:

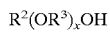

wherein $R^2$ is methyl; $R^3$ is ethylene; x has the value from about 10 to about 225, with phosgene to form a chloroformate having the formula:

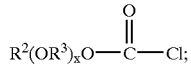

b) combining an anthranilic acid or derivative thereof having the formula:

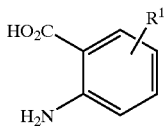

wherein each $R^1$ unit is hydrogen or methyl; and poly N-vinylpyridine to form a substrate reactive admixture;

c) adding to said substrate reactive admixture formed in step (b) said chloroformate from step (a) to form a benzoxazin-4-one conjugate having the formula:

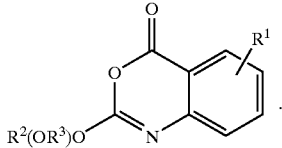

31. A process according to claim 30 wherein each step is conducted in the presence of a solvent selected from the group consisting of dichloromethane, toluene, and mixtures thereof.

* * * * *